United States Patent
Buess et al.

(10) Patent No.: US 11,116,421 B2
(45) Date of Patent: Sep. 14, 2021

(54) METHOD FOR CONDITIONING A BREATHING TUBE

(71) Applicant: ndd Medizintechnik AG, Zurich (CH)

(72) Inventors: Christian Buess, Horgen (CH); Erich Kleinhappl, Waedenswil (CH)

(73) Assignee: ndd Medizintechnik AG, Zurich (CH)

( * ) Notice: Subject to any disclaimer, the term of this patent is extended or adjusted under 35 U.S.C. 154(b) by 524 days.

(21) Appl. No.: 15/953,233

(22) Filed: Apr. 13, 2018

(65) Prior Publication Data

US 2018/0333074 A1    Nov. 22, 2018

(30) Foreign Application Priority Data

May 16, 2017    (EP) .................................... 17171300

(51) Int. Cl.
| | |
|---|---|
| *A61B 5/087* | (2006.01) |
| *A61B 8/08* | (2006.01) |
| *B29D 23/00* | (2006.01) |
| B29L 23/00 | (2006.01) |
| B29C 53/16 | (2006.01) |
| A61M 16/08 | (2006.01) |

(52) U.S. Cl.
CPC ............... *A61B 5/087* (2013.01); *A61B 8/48* (2013.01); *B29D 23/00* (2013.01); *A61M 16/0875* (2013.01); *A61M 2205/366* (2013.01); *A61M 2205/368* (2013.01); *A61M 2209/06* (2013.01); *B29C 53/16* (2013.01); *B29L 2023/007* (2013.01)

(58) Field of Classification Search
CPC ................................................. A61M 16/0875
See application file for complete search history.

(56) References Cited

U.S. PATENT DOCUMENTS

| | | | |
|---|---|---|---|
| 5,067,492 A | 11/1991 | Yelderman et al. | |
| 5,419,326 A | 5/1995 | Harnoncourt | |
| 6,978,657 B1 * | 12/2005 | Baumann ............. | G01N 1/2214 73/28.04 |
| 7,299,711 B1 * | 11/2007 | Linker ................. | G01N 1/2214 73/863.23 |
| 7,635,339 B2 * | 12/2009 | Harnoncourt .......... | A61B 5/087 600/529 |
| 2013/0032152 A1 | 2/2013 | Reuterholt et al. | |
| 2016/0128608 A1 | 5/2016 | Buess et al. | |

FOREIGN PATENT DOCUMENTS

| | | |
|---|---|---|
| CN | 102655807 A | 9/2012 |
| CN | 105581796 A | 5/2016 |
| DE | 4039215 A1 | 6/1992 |
| EP | 1632178 A1 | 3/2006 |
| EP | 3017768 A1 | 5/2016 |
| WO | 9324810 A1 | 12/1993 |

* cited by examiner

*Primary Examiner* — LaToya M Louis
(74) *Attorney, Agent, or Firm* — McCoy Russell LLP

(57) ABSTRACT

A method for conditioning a breathing tube for use in lung function diagnostics and a breathing tube made by such a method. This method is characterized by heating at least a section of a fully assembled breathing tube by a heating source to a temperature of at least 40° C., wherein heating is performed during a first time period, the first time period lasting between 0.1 seconds and 5 seconds wherein the section includes at least one window covered by a mesh.

11 Claims, 1 Drawing Sheet

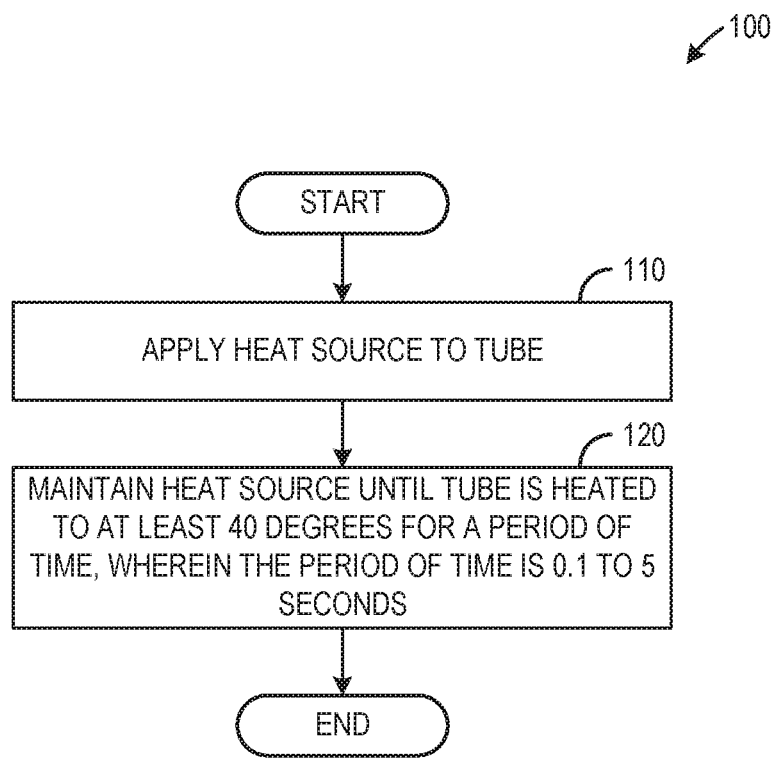

METHOD FOR CONDITIONING A BREATHING TUBE

CROSS-REFERENCE TO RELATED APPLICATIONS

The present application claims priority to European Patent Application No. 17 171 300.1, entitled "METHOD FOR CONDITIONING A BREATHING TUBE," filed on May 16, 2017, the entire contents of which is incorporated herein by reference in its entirety for all purposes.

DESCRIPTION

The instant present disclosure relates to a method for conditioning a breathing tube for use in lung function diagnostics, the breathing tube having a structure conditioned by heating at least a section of the fully assembled breathing tube by a heating source as well as a breathing tube that can be made by such a method.

TECHNICAL FIELD

EP 3 017 768 A1 describes a breathing tube for use in lung function diagnostics that comprises two windows through which ultrasonic waves can be passed in order to measure the flow of gas flowing through the breathing tube. These windows are covered by a mesh that serves for reducing any gas flow through the windows from the interior of the breathing tube to the exterior thereof. Furthermore, the mesh reduces airflow turbulences in the region of the windows.

BACKGROUND AND SUMMARY

The inventors noted that this mesh corrugates during the manufacturing process, even if it has been fully planar at an earlier step of the manufacturing process. However, a corrugated mesh distorts ultrasonic measurements of the gas flow within a corresponding breathing tube since the distance between the first window of the breathing tube and the second window of the breathing tube varies indefinitely due to the corrugations of the mesh.

It is an object of the instant present disclosure to provide a method for conditioning a breathing tube enabling a more exact determination of the flow of a gas flowing through the breathing tube by an ultrasonic measurement than the breathing tubes manufactured according to methods known from prior art do.

This object is achieved by a method for conditioning a breathing tube by heating at least a section of a fully assembled breathing tube by a heating source to a temperature of at least 40° C., wherein heating is performed during a first time period, the first time period lasting between 0.1 seconds and 5 seconds, wherein the section comprises at least one window covered by a mesh. A corresponding breathing tube typically comprises two windows that are each covered by a mesh. The breathing tube is intended to be used in lung function diagnostics.

The term "lung function diagnostics" refers to any kind of the analysis of breath gas (i.e., the analysis of gas inhaled or exhaled by a person) to determine the lung function of a patient, in particular all applications of spirometry, gas washout measurements, gas dilution measurements, or gas diffusion measurements. Typical parameters determined by lung function diagnostics are forced vital capacity (FVC), forced expiratory volume in 1 second (FEV1), FEV1/FVC ratio (FEV1%), forced expiratory flow (FEF), forced inspiratory flow 25-75% or 25-50%, peak expiratory flow (PEF), tidal volume (TV), total lung capacity (TLC), diffusing capacity (DLCO), maximum voluntary ventilation (MVV), functional residual capacity (FRC), and/or lung clearance index (LCI). The instantly described and/or claimed breathing tube is intended to be used for determining any of these parameters in spirometry or to be used for any other kinds of lung function diagnostics without specific limitation.

The method comprises a heating step in which at least a section of a fully assembled breathing tube is heated by a heating source to a temperature of at least 40° C. Thereby, the section comprises at least one window covered by a mesh. Thus, at least the mesh is heated to at least 40° C. Due to this thermal treatment, the mesh is automatically straightened without mechanically acting upon the mesh. Thus, a flattened mesh results so that a distance between a first window covered by said mesh and a second window covered by an equivalent mesh is not dependent on any corrugations of the mesh, but is rather stably invariable.

In an embodiment, only the mesh reaches the beforementioned temperature, whereas other sections of the breathing tube keep a lower temperature.

The mesh can comprise or can be made entirely of the same material as the rest of the breathing tube, i.e., the breathing tube body. Appropriate materials for the breathing tube body are polyethylene (PE), polypropylene (PP), acrylonitrile butadiene styrene (ABS), polyether ether ketone (PEEK), polycarbonates (PC), polystyrene (PS), polyethylene terephthalate (PET), polyethylene terephthalate glycol (PETG), polyamide (PA), polyacetal (polyoxymethylene, POM), as well as blends and copolymers thereof. A copolymer of PE and PP is particularly appropriate.

In an embodiment, the mesh can comprise or can be made entirely of a material that is different from the material used for the flow tube body. Appropriate materials for the mesh are polyesters, PA, PET, PP, chlorotrifluoroethylene (CTFE), ethylene tetrafluoroethylene (ETFE), as well as blends and copolymers thereof. In an embodiment, the mesh essentially consists of only a single material (which can be a copolymer of different plastic materials or a composite material comprising reinforcing elements).

The mesh is typically manufactured separately from and/or prior to the breathing tube body. Such a pre-manufactured mesh can then be fixed into an also pre-manufactured breathing tube body, e.g., by gluing or bonding the mesh into the body. In an embodiment, the mesh is inserted into a mold being used for manufacturing the breathing tube body by injection molding. The breathing tube body is then injection-molded around the mesh, i.e. the mesh is fixed to the breathing body by insert molding, wherein the breathing tube body is produced around the mesh so as to obtain a breathing tube with windows covered by the mesh.

To give an example, the mesh can consist of a woven material that is stretched at the end of the manufacturing process of the mesh.

In an embodiment, the breathing tube that is conditioned can be described as having a breathing tube body; a first window located on a first side of the breathing tube body, the first window serving for allowing ultrasonic waves to pass from an exterior of the breathing tube body to an interior of the breathing tube body and vice versa; and a second window located on a second side of the breathing tube body, wherein the second side is opposite the first side, the second window serving for allowing ultrasonic waves to pass from an interior of the breathing tube body to an exterior of the breathing tube body and vice versa (ultrasonic waves always pass in both directions). Thereby, the first window and the second window are each fully covered by a mesh.

If the mesh reaches, by heating the breathing tube in the heating step to a temperature of the subsequently listed temperatures, a temperature of at least 40° C., in particular at least 45° C., in particular at least 50° C., in particular at least 55° C., in particular at least 60° C., in particular at least 65° C., in particular at least 70° C., in particular at least 75° C., in particular at least 80° C., in particular at least 85° C., in particular at least 90° C., in particular at least 100° C., in particular at least 105° C., in particular at least 110° C., in particular at least 115° C., in particular at least 120° C., the mesh is automatically straightened due to a molecular reorganization of the material of which the mesh is made. The materials that are typically used for producing the mesh are already formable at such a temperature.

To avoid complete melting of the mesh, the temperature of the mesh that is achieved during the heating step is, in an embodiment, chosen such that the breathing tube is only heated to a temperature that is at least 10° C. lower than a lower temperature of the melting range of the mesh. If, e.g., the mesh is made of low density polyethylene (LDPE) or high-density polyethylene (HDPE), it has a melting range of 130 to 145° C. Then, the heating step is performed such that the temperature of the mesh does not become higher than 120° C. Thereby, it is assured that the mesh is formable and can be straightened by the thermal treatment, but still stays in its solid state.

In an embodiment, the temperature to which the breathing tube is heated is at least 15° C., in particular at least 20° C., in particular at least 25° C., in particular at least 30° C., in particular at least 35° C., in particular at least 40° C., in particular at least 45° C., in particular at least 50° C., in particular at least 55° C., in particular at least 60° C., in particular at least 65° C., in particular at least 70° C. lower than a lower temperature of a melting range of the mesh.

A appropriate temperature range to which the section of the breathing tube is heated during the thermal treatment is, in an embodiment, a temperature range of 40° C. to 120° C., in particular 45° C. to 115° C., in particular 50° C. to 110° C., in particular 55° C. to 105° C., in particular 60° C. to 100° C., in particular 65° C. to 95° C., in particular 70° C. to 90° C., in particular 75° C. to 85° C., in particular 40° C. to 80° C.

To achieve a particular appropriate molecular reorganization within the material of the mesh, the temperature of the mesh that is achieved during the heating step is, in an embodiment, chosen such that the mesh of the breathing tube is heated to a temperature that is at least as high as a glass transition temperature of the mesh. If, e.g., the mesh is made of high-density polyethylene (HDPE), it has a glass transition temperature of 70° C. Then, the heating step is performed such that the temperature of the mesh is at least 70° C. Thereby, it can be particularly well assured that the mesh is formable and can be straightened by the thermal treatment.

In an embodiment, the temperature to which the breathing tube is heated is at least 5° C., in particular at least 10° C., in particular at least 15° C., in particular at least 20° C., in particular at least 25° C., in particular at least 30° C., in particular at least 35° C., in particular at least 40° C., in particular at least 45° C., in particular at least 50° C., in particular at least 55° C., in particular at least 60° C., in particular at least 65° C., in particular at least 70° C. higher than the glass transition temperature of the mesh.

In an embodiment, the heating source is a hot fluid source or a radiation source. An appropriate hot fluid source is a hot air source such as a hot air blower. Depending on the material of the mesh, an appropriate radiation source is an infrared radiation source or a microwave radiation source. Typically, infrared radiation is more appropriate to heat plastic materials than microwave radiation is.

While liquid heating media could well be applied within the instantly claimed method, gaseous heating media are generally even more appropriate. Thereby, hot air is a cheaply and easily available hot fluid that can well be used as heating medium within the instantly claimed method.

In an embodiment, the heating source emits a heating medium having a temperature of 180° C. to 230° C., in particular of 185° C. to 225° C., in particular of 190° C. to 220° C., in particular of 195° C. to 215° C., in particular of 200° C. to 210° C. Alternatively, an (infrared) radiation could be used as heating medium that enables a heat input into the breathing tube that corresponds to the heat input of a (fluid) heating medium having a temperature in any the before-mentioned temperature ranges.

In an embodiment, the heating is performed during a first time period. Thereby, the first time period lasts between 0.1 seconds and 5 seconds, in particular 0.2 seconds and 4 seconds, in particular 0.3 seconds and 3 seconds, in particular 0.4 seconds and 2 seconds, in particular 0.5 seconds and 1 second. To achieve such a first time period, a relative movement between the breathing tube and the heating source is well appropriate. To give an example, the breathing tube can be moved through an area in which a hot fluid such as hot air is flowing.

In an embodiment, the breathing tube is transferred into a packaging directly after the heating. It is then sealed within the packaging and is allowed to cool to ambient temperature in the packaging. Thus, the heating step of the instantly claimed method can be performed directly prior to packaging the breathing tube. In such a case, no additional time-consuming method step need to be performed for conditioning the breathing tube.

In an embodiment, the packaging comprises a perforation so that air can enter and exit the packaging even if the breathing tube is sealed therein. In another embodiment, the breathing tube is sealed within the packaging in an air-tight manner.

In an embodiment, the packaging is a plastic bag like bags that are already commonly used in prior art for packaging breathing tubes.

In an aspect, the instant present disclosure also relates to a breathing tube for use in lung function diagnostics that can be obtained by a method according to the preceding explanations. Such a breathing tube is characterized by plane (smooth) meshes covering the windows of the breathing tube and serving for guiding ultrasonic waves through them. Due to the plane meshes of such a breathing tube, it enables very precise and reliable measurements by ultrasound of the flow of a gas flowing through the breathing tube.

All embodiments described with respect to the instantly claimed method can be combined in any desired way. Furthermore, they can be transferred in any combination to the claimed breathing tube.

BRIEF DESCRIPTION OF THE DRAWINGS

FIG. 1 is a flow chart of an exemplary method 100 for conditioning a breathing tube for lung function diagnostics.

EXEMPLARY EMBODIMENT

To assess the effects of the conditioning method described herein, comparative measurements have been performed.

First, the flow of gas flowing through a breathing tube according to prior art was determined in a lung function diagnostics device with ultrasound under standardized conditions. Thereby, the breathing tube had two windows on opposite sides of the breathing tube, wherein both windows were covered by a mesh (the breathing tube is described in more detail in EP 3 017 768 A1). The flow of gas in 24 different breathing tubes was measured, wherein each breathing tube was measured four times. A standard deviation was calculated for each breathing tube. The average of these standard deviations was calculated to be approximately ±0.85% (Comparative Example).

Afterwards, an identically configured breathing tube was examined that was additionally conditioned as shown in FIG. 1, by heating at step 110 both meshes to a temperature of more than 40° C. at step 120 by applying a flow of hot air (ca. 200° C.) for a period of ca. 0.8 seconds to the breathing tube in the area of the meshes. The flow of air flowing through this conditioned breathing tube was examined under identical conditions like in the Comparative Example. The flow of gas in 24 different breathing tubes was measured, wherein each breathing tube was measured four times. A standard deviation was calculated for each breathing tube. The average of these standard deviations was calculated to be approximately ±0.42% (Example according to the claimed present disclosure).

Thus, the standard deviation was decreased by the factor 2 in the Example according to the claimed present disclosure due to the conditioning step.

Additionally, the meshes of the breathing tube have been optically inspected prior to and after the conditioning step in the Example according to the claimed present disclosure. The mesh appeared to be much more flattened after the conditioning step. It had less wrinkles or corrugations than before the conditioning step. Thus, the conditioning step resulted in a straightened mesh that enabled more reliable measurements of the flow of gas flowing through the breathing tube.

The mesh kept its straightened form also during prolonged storage under defined conditions. Stability measurements under varying storage conditions in a temperature range of −20° C. to +50° C. at a relative humidity of 10% to 90% did not alter the corrugation of the mesh after the breathing had been conditioned. Rather, the mesh of the conditioned breathing tube kept smooth.

The invention claimed is:

1. A method for conditioning a breathing tube for use in lung function diagnostics, comprising heating, by a heating source, at least a section of a fully assembled breathing tube prior to use to a temperature of at least 40° C., wherein the section comprises at least one window covered by a mesh, wherein the heating is to a temperature at which the mesh undergoes molecular reorganization, wherein the heating is only performed during a first time period, the first time period lasting between 0.1 seconds and 5 seconds, and wherein the mesh is entirely made of a material chosen from the group consisting of polyethylene, polypropylene, acrylonitrile butadiene styrene, polyether ether ketone, polycarbonates, polystyrene, polyethylene terephthalate, polyethylene terephthalate glycol, polyamide, polyacetal, polyesters, chlorotrifluoroethylene, ethylene tetrafluoroethylene, and copolymers thereof.

2. The method according to claim 1, wherein the section of the breathing tube is heated to a temperature that is at least 10° C. lower than a lower temperature of a melting range of the mesh.

3. The method according to claim 1, wherein the section of the breathing tube is heated to a temperature that is at least as high as a glass transition temperature of the mesh.

4. The method according to claim 1, wherein the heating source is a hot fluid source or a radiation source.

5. The method according to claim 4, wherein the hot fluid source is a hot air source.

6. The method according to claim 1, wherein in that the heating source emits a heating medium having a temperature of 180° C. to 230° C. or a radiation enabling a heat input into the breathing tube that corresponds to a heat input of the heating medium having a temperature of 180° C. to 230° C.

7. The method according to claim 1, wherein the first time period lasts between 0.2 seconds and 4 seconds.

8. The method according to claim 1, wherein the breathing tube is transferred into a packaging directly after the heating, is sealed within the packaging, and is allowed to cool to ambient temperature in the packaging.

9. The method according to claim 8, wherein the packaging is a plastic bag.

10. The method of claim 1, wherein the molecular reorganization straightens the mesh.

11. A fully assembled breathing tube for use in lung function diagnostics, the breathing tube having a structure conditioned by heating at least a section of the fully assembled breathing tube by a heating source to a temperature of at least 40° C., wherein the section comprises at least one window covered by a mesh, wherein the heating is only performed during a first time period, the first time period lasting between 0.1 seconds and 5 seconds, and wherein the mesh is entirely made of a material chosen from the group consisting of polyethylene, polypropylene, acrylonitrile butadiene styrene, polyether ether ketone, polycarbonates, polystyrene, polyethylene terephthalate, polyethylene terephthalate glycol, polyamide, polyacetal, polyesters, chlorotrifluoroethylene, ethylene tetrafluoroethylene, and copolymers thereof.

* * * * *